Figure 2:
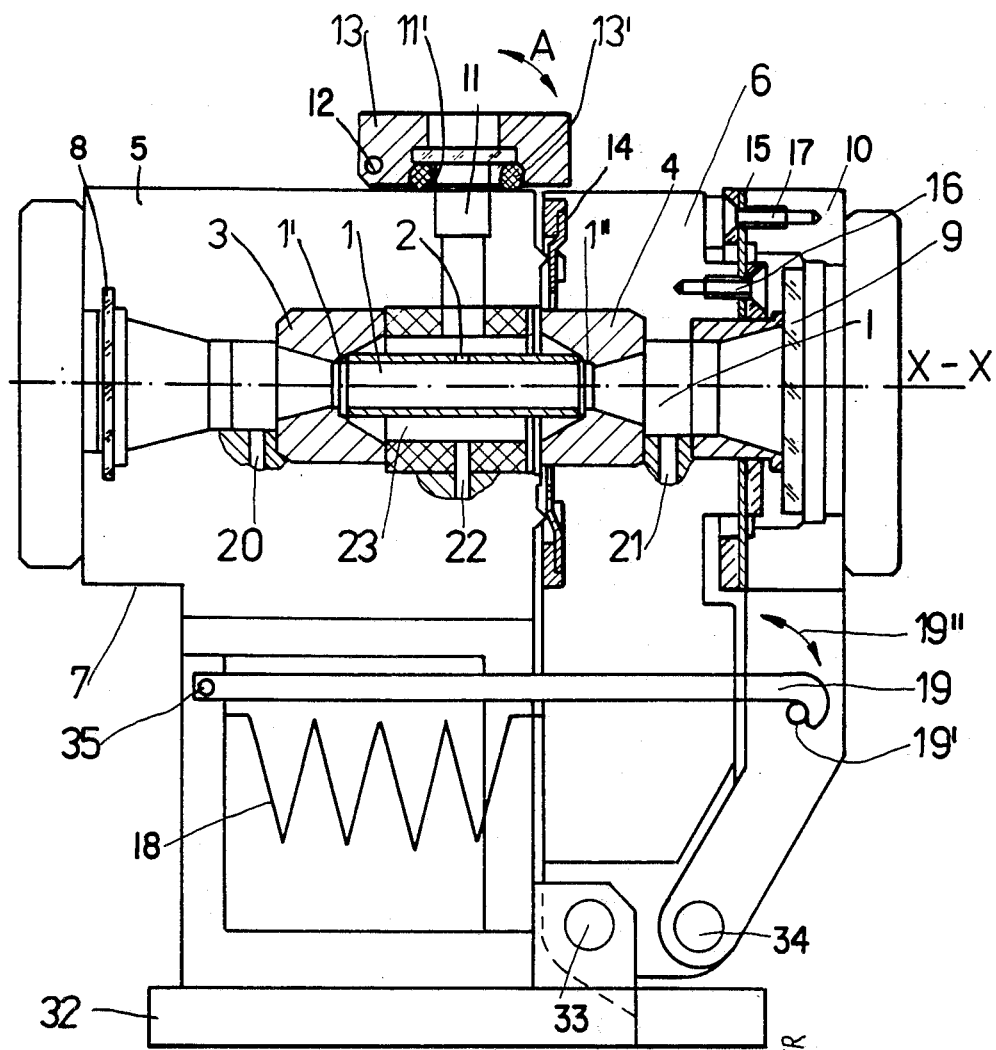

United States Patent [19]

Falk

[11] Patent Number: 4,660,976
[45] Date of Patent: Apr. 28, 1987

[54] METHOD AND DEVICE FOR ELECTROTHERMAL ATOMIZATION OF A SAMPLE MATERIAL

[75] Inventor: Heinz Falk, Berlin, German Democratic Rep.

[73] Assignee: Jenoptik Jena GmbH, Jena, German Democratic Rep.

[21] Appl. No.: 605,931

[22] Filed: May 1, 1984

[51] Int. Cl.[4] ............................................. G01N 21/74
[52] U.S. Cl. ...................................... 356/312; 356/244
[58] Field of Search ............................... 356/312, 244

[56] References Cited

U.S. PATENT DOCUMENTS 4,098,554  7/1978  Huber et al. ...................... 356/312

FOREIGN PATENT DOCUMENTS 0036087  3/1977  Japan ............................... 356/312
2102589  2/1983  United Kingdom ............... 356/312

OTHER PUBLICATIONS

Rapperport et al., *Rev. Sci. Instr.*, vol. 41, No. 8, Aug. 1970, pp. 1168–1171.

Perkin—Elmer HGA—500 brochure, Feb. 14, 1979.

*Primary Examiner*—F. L. Evans
*Assistant Examiner*—Joel L. Harringa
*Attorney, Agent, or Firm*—Jordan and Hamburg

[57] ABSTRACT

The invention relates to a method and device for electrothermal atomization of a sample material, particularly for use in atomic absorption or atomic fluorescence spectroscopy in which an atomizing apparatus including a graphite tube sealed towards ambience is connected to a pressure gas source. The gas inlets provided in said atomizing apparatus serve to produce a symmetrical configuration of an atomized sample material cloud, the atomization of the sample material is acheived by a respective temperature increase which is combined with a pressure gas increase at least during a period of temperature increase. The relation between the starting pressure of the gas and the final pressure of the gas is substantially equal to the relation between the starting temperature and the final temperature. The device used for carrying out the method of the invention includes a control system for control of the temperature and the pressure in said atomization apparatus.

6 Claims, 2 Drawing Figures

METHOD AND DEVICE FOR ELECTROTHERMAL ATOMIZATION OF A SAMPLE MATERIAL

The invention relates to a method and device for electrothermal atomization of a sample material to be analysed particularly for use in atomic absorption or atomic fluorescence spectroscopy.

Electrothermal atomizers (hereinafter ETA) serve to excite liquid or solid sample materials to a state of substantially entire dissociation into their atomic components.

Previous electrothermal atomizers require a finite time $t_1$ (formation time) for a complete evaporation and atomization of a sample material and the released atoms reside only a definite time $t_2$ ($t_2$ = retention time) in an analysis volume a zone within an atomization hollow apparatus.

The measuring signal obtained from a spectroscopic sample signal will be the greater with a given sample material, the lower $t_1$ and the higher $t_2$ can be made.

It is known from C. L. Chakrabati et al. in Anal. Chem. 52, 167 (1980) to use extremely high heating rates for the electrothermal atomizer of the order of about 10 KV/sec. to obtain a ratio of $t_1 < < t_2$.

This device is disadvantageous since, apart from being expensive, it is limited by the setting times for the thermodynamic equilibrium between the heated atomizer body walls and the sample material, and the carrier gas used and, hence, does not permit an increase of $t_2$ and therefore of the integral of time for the signal peak.

It is an object of the present invention to obviate the above disadvantages.

It is a further object of the present invention to provide a method and device for electrothermal atomization which increases the retention time of an atomized sample material in such a device and which enhances the detection efficiency and the precision thereof.

It is still a further object of the present invention to provide a method and device for electrothermal atomization which, in addition to the above objects, permits to investigate an increased amount of sample material at a simultaneous reduction of the sample losses.

It is still a further object of the invention to provide a method and device for electrothermal atomization which increases the residence time of an atom cloud of a sample material in the investigation region in that the local expansion of said atom cloud in the course of temperature increase is limited.

These and other objects are realised in a method for electrothermal atomization of a sample material, comprising a step of drying and incinerating of a sample material in a protective gas followed by the step of atomization of the sample material and converting the latter into an atomic sample material cloud by a temperature increase which at least for the period of atomization is combined with an increase of the pressure of the protective gas symmetrically applied to the sample material cloud volume.

The relation between the starting pressure and the end pressure is, at least, equal to the relation between the starting temperature and the end temperature.

Advantageously, the rise of the pressure of the protective gas during the atomizing phase is maintained for a longer period than for the period of the temperature increase.

The objects of the invention are further realised by a device for electrothermal atomization of a sample material which comprises an excitation tube framed by electrodes. Said tube is surrounded by a protective gas. The tube framed by the electrodes is located in a hollow tripartite body.

One electrode of said electrodes is contained in a first part of said tripartite hollow body, the other electrode of said electrodes is contained in a second part of said tripartite hollow body. Both parts are hermetically and detachably connected to one another. The first part of the tripartite hollow body is provided with a radial bore hole that extends from the exterior to the interior of the hollow body at right angles to a common axis of the tube and of the hollow body. The bore hole is in alignment with an opening in the center portion of the tube.

Furthermore, the interior of the tripartite hollow body is connected to a protective gas source via a first, a second and a third bore through the hollow body wall.

The first bore and the second bore are in the vicinity of the front and rear portion, respectively, of the tube, whereas the third bore is directed to the central portion of the tube.

The side of the second part of the tripartite hollow body facing away from the tube is connected to a third part of the tripartite hollow body. The connection between the second and the third part is hermetically and releasably via a pivot provided in the second part of the hollow body.

A latch is pivotally secured to the first part of the tripartite hollow body housing and establishes a close connection between the second and the third part.

The first and the third part of the tripartite body are provided with a window each. The bore hole is tightly closed by a removeable lid on the first part of the tripartite body.

Means are provided to permit a controlled protective gas feed from at least one additional pressure gas container to the interior of the hollow body and to the tube, respectively.

In order that the invention may be more readily understood reference is made to the accompanying drawings which illustrate diagrammatically and by way of example one embodiment thereof and where the FIG. 1 is a schematic and partly sectional view of an electrothermal atomizer (ETA) in an atomizing apparatus and FIG. 2 a protective and pressure gas feeding system for the ETA of FIG. 1.

In FIG. 1 an apparatus for electrothermal atomization of a sample material is constituted of a housing 7 comprising a first part 5, a second part 6 and a third part 10, which parts are fitted together to enclose an interior elongated channel I having an axis X—X. In a bulged central portion of said channel I an open ended graphite tube 1 is arranged the axis of which substantially coincides with the axis X—X.

The graphite tube 1 is the atomizer cell of the electrothermal atomizing apparatus.

The graphite tube 1 is provided with a first radial bore 2 substantially at the mid-point of the length of the tube 1 which bore 2 is in alignment with a second radial bore 11 extending from an opening 11' in the outer wall of the housing 7 of the first part 5 up to the bulged portion of the channel I. The opening 11' is sealed by a lid 13 which can be tilted about an axis 12 in the directions indicated by a double arrow A to open or close the opening 11'.

A rubber ring 13' serves as an airtight seal for the lid 13 when closed. The first radial bore 2 provides an access for introducing a sample material into the graphite tube 1.

The edges of the open-ended portions 1', 1" of the graphite tube 1 are in close contact with a first electrode 3 which abuts against the interior wall of the housing part 5 and a second electrode 4, respectively, which abuts against the interior wall of the housing part 6.

Both electrodes 3 and 4 have sufficiently large openings of substantially the size of the graphite tube 1 diameter to permit passage of diverse radiations involved in the course of sample material analysis.

The openings of the electrodes 3 and 4 are concentrically about the axis X—X.

A power supply (not visible) is connected via not visible lines to the electrodes 3 and 4 to flow electric current through the graphite tube 1 to heat it to an elevated temperature sufficient to atomize a sample material.

The housing 7 is mounted on a base 32 to which the housing part 5 is non-displaceably secured. The housing part 6 is hinged to the part 5 via a pivot axis 33 located in the base 32.

An annular rubber seal 14 surrounds the channel I in the region of contact of the opposing faces of part 5 and 6 so that an airtight but resilient connection is established between the opposing faces of parts 5 and 6, which is secured by a latch 19 described hereinafter.

The housing part 6 is connected to the housing part 10 via a further rubber ring 15 between the opposing faces of parts 10 and 6.

The rubber ring 15 again surrounds the channel I.

The housing part 10 is hinged to the bottom portion of part 6 in a pivot 34 and is screwed via its top portion by screws 16 and 17 to the housing part 6 and vice versa.

The lever 19 is hinged to a pivot 35 via one end portion which is provided at the base 32 in the vicinity of the part 5 and constitutes a lock between part 5 and part 10 when the lever 19 is engaged in a pin 19' on the part 10 thus tightly pressing the opposing faces of the parts 5 and 4 and 6 and 10, respectively, against one another what, in turn, secures a close electrical contact between the electrodes 3 and 4 and the graphite tube 1.

The lock 19 is only opened against the tension of the spring force of a pressure spring 18 when the graphite tube 1 has to be exchanged for another one.

The end portions of the channel I which extends in alignment with the graphite tube 1 and the electrodes 3 and 4 openings about the optical axis X—X through the parts 5, 6 and 10, are closed to the exterior via windows 8 and 9, respectively.

These windows 8 and 9 render the channel I airtight by resilient means and locking rings not specifically designated and described.

The channel I is provided with three further radial bores 20, 21 and 22. These bores 20, 21, 22 are connected via not visible flanges to a gas feeding system (FIG. 2) to ducts 20', 21', and 22'. The radial bores 20 and 21 open into the channel I between the windows 8 and 9, respectively, and the respective electrodes 3 and 4, adjacent to the latter.

The radial bore 22 opens into the bulged portion, namely a cavity 23 limited by the channel I wall and the outer wall of the graphite tube 1, on the one hand and by the electrode 3 and 4 portions facing one another, on the other hand.

Furthermore, the parts 5, 6 and 10 are provided with a water-cooling system for circulation of a cooling liquid omitted in the drawing for the sake of clarity.

In FIG. 2, a protective gas and carrier gas, respectively, feed system is shown comprising a protective or carrier gas supply source 25, a pressure gas supply source 27 and a pressure/temperature control unit 31 which is connected via a not visible line to a not visible temperature feeler in the atomizer device (FIG. 1) for detecting the temperature thereof and via a further not visible control line to the electric power source.

The ducts 20' and 21' are connected via a valve 24 in a piping 35 to the protective gas supply source 25, and via a valve 26 to the pressure gas source 27.

The duct 22' is connected either to the protective gas source 25 via a valve 29 or to the pressure gas source 27 via a valve 28.

Furthermore a valve 30 is inserted into the piping 35 between the valve 28 and the pressure gas source 27.

The valve 30 is operatively connected to the pressure/temperature control unit 31.

In operation, a sample material to be analysed is inserted via the open borehole 11 and through the opening 2 into the graphite tube 1 of the electrothermal atomizer.

In a first step the electrodes 3 and 4 produce a heating of the graphite tube 1 and of the inserted sample material to a temperature which effects a drying and incineration of the sample material to remove any interfering components.

To this end an "internal" gas flow is established which via the inlets 20 and 21 flows through the electrode 3 and 4 openings into the graphite tube 1 and through the outlet 2 (opening 2) and the bore hole 11 to the outside since the lid 13 is open during the drying and incineration step. In this manner the windows 8 and 9 are prevented from becoming inoperative due to possible condensates since the vapor is deducted from the tube 1 to the outside. Since the valves 24 and 29 are open and the valve 26 is closed during the drying step the carrier gas source 25 is connected to the inlets 20 and 21 via the valves 24, and to the inlet 22 via the valve 29.

The latter connection constitutes an "external" gas flow via the inlet 22, the cavity 23 and the "outlet" 11 (bore hole 11) which also serves to prevent an oxidation of the heated parts of the atomizer.

It is selfunderstood that the valve 28 is closed so that the pressure gas source 27 is disconnected from the gas flow system.

In a second step the atomization of the sample material is carried out, which starts with sealing the opening 11' by closing the lid 13, and by opening the valves 26 and 28 and closing the valves 24 and 29 so that the carrier gas flow is disconnected.

Then the temperature is increased by about 1000° K./Sec. starting from a temperature of 1000° K. which is achieved by energizing the electrodes 3 and 4 via the not shown power source that, in turn, is controlled by operation of the control unit 31 (via the not shown control line to the power source). At a suitable moment of the atomization step the valve 30 is opened via operation of the control unit 31. The gas pressure from the source 27 compresses via the duct 22 and the ducts 20 and 21 the atomized sample material cloud in the graphite tube 1 so that the cloud takes a symmetrical configuration (not shown).

Under the temperature conditions specified hereinabove, the pressure in the graphite tube is increased from about 100 K Pa to about 180 K Pa in one second. Since the residence time of analyte atoms which is defined by the diffusion in the sample material cloud is about 0.5 to 1 second an entire pressure increase of about 100 to 200 KPa/sec. is necessary to compensate for this loss. Therefore, an entire pressure increase of about 200 to 300 KPa/sec. will be suitable for the present example. This pressure increase in the graphite tube 1 is effected by operation of the valve 30 via the control unit 31.

The atomized sample material cloud (not shown) in the graphite tube 1 is evaluated by suitable means through the window 8 and 9 what finalizes the sample material investigation. Then the valve 30 is closed and the lid 9 is opened and the steps as having been described hereinbefore can be executed for a next sample material investigation.

The invention is not restricted to the above embodiment.

It is feasible to insert a further valve 36 into the piping between the inlet 22 and the pressure gas system 27 which serves to control the configuration of the cloud via the pressure in the graphite tube 1.

The control unit 31 which controls both, temperature and pressure, is any suitable means, manually and/or electrically operable.

The valves 24, 26, 28, 29 and 30 are embodied by valves manually operable or by servo-motors via respective displacement means.

The valves 28 (and 36) are very sensitive valves which permit a controlled pressure and speed of the pressure gas flow in dependence on the pressure in the gas source 27.

The temperature in the atomizer tube 1 is controlled by the not shown temperature feeler in the tube 1 in cooperation with the control unit 31. Alternatively, the temperature is determined by an algorithm which is not an object of the present invention. In the latter instance the temperature feeler (not visible) can be dispensed with. Such a temperature control is disclosed, for example, in the DD WP No. 2008235, published June 15, 1983.

I claim:

1. A method for electrothermal atomization of a sample material in an electrothermal atomization apparatus including a protective and pressure gas source comprising the steps of
    heating the sample material to a temperature below the atomizing temperature to dry and incinerate said sample material under a protective gas to remove interfering components,
    heating the dried and incinerated sample material by temperature increase to an atomizing temperature to produce a sample material cloud and simultaneously applying a gas pressure to the sample material cloud by a gas pressure increase to produce a symmetrical sample material cloud configuration in said electrothermal atomization apparatus, wherein the relation of the starting pressure of the gas to the final pressure of the gas substantially is equal to the relation of starting temperature to the final temperature during the step of heating the dried and incinerated sample material.

2. A method for electrothermal atomization as claimed in claim 1, wherein the rise of the gas pressure is maintained for a longer period than the period for the temperature increase.

3. A device for electrothermal atomization of a sample material comprising
    a tripartite longitudinal atomization hollow body having
    a longitudinal axis of symmetry X—X,
        said hollow body being subsequently composed of a first part, a second part, and a third part,
    a channel extending through said first part,
    said second part and said third part symmetrically about said axis X—X,
        said channel end portions being sealed to the exterior by a first window and a second window, respectively,
    an open ended atomizer tube,
    a first electrode having a central bore,
    a second electrode having a central bore,
        said atomizer tube being arranged in a central bulged out portion of said channel, concentrically to said axis X—X,
        said first electrode being in close electrical contact to the one end portion of said atomizer tube in said first part,
        said second electrode being in close electrical contact to another end portion of said atomizer tube in said second part,
        said atomizer tube, the central bores through said first and said second electrode being concentrically to said axis X—X,
        said bulged out portion forming a cavity limited by the outer wall of said atomizer tube and the channel wall,
    a first radial bore extending from the exterior to said cavity,
    a second radial bore being provided in the mid-portion of the wall of said atomizer tube,
        said first and said second radial bore being in alignment,
    means for airtight sealing said first radial bore to the outside,
        said first and said second radial bore being for introducing said sample material,
    first connection means for airtight connection of said first part to said second part,
    second means for airtight connection of said second part to said third part,
    a third radial bore and a fourth radial bore extending from the exterior to said channel in the neighborhood of said first and said second electrode, respectively,
    a fifth radial bore extending from said exterior to said cavity in alignment and opposition to said first radial bore,
    a carrier gas and pressure gas system having a first, a second, and a third connection piece in a piping,
        said first and said third connection piece being connected to said third and to said fourth radial bore, respectively,
        said second connection piece being connected to said fifth bore, a carrier gas source,
    a pressure gas source, both being provided in said gas system, first control means for controlled variation of
        the gas flow from said carrier gas source to said channel, said first control means being provided in said piping, second control means for a controlled variation of pressure gas flow from said pressure gas source to said channel, said second control means being provided in said piping, a gas pressure and temperature control means being connected to said second control means for a controlled variation of the pressure gas flow from said pressure gas source to said channel and said cavity, respectively, via said piping and said third fourth and fifth bore, respectively.

4. A device as claimed in claim 3, wherein said first control means for a controlled variation of the gas flow comprises a first valve, a second valve and a third valve, the first valve is inserted in the piping between the protective gas source and said first and said third connection piece, the second valve is inserted into the piping between said first valve and said second valve, said third valve is inserted into the piping between said protective gas source and said second connection piece.

5. A device as claimed in claim 4, wherein said second means for a controlled variation of the pressure gas flow comprises a fourth and a fifth valve, said fourth valve being inserted into said piping between said first, second and third connection piece, on the one hand, and the gas pressure source on the other hand, said fifth valve is inserted into the piping between said fourth valve and said gas pressure source.

6. A device as claimed in claim 5, wherein said pressure gas source exercises a defined pressure via the first, second and third connection pieces upon an atomized sample material cloud in said graphite tube.

* * * * *